United States Patent [19]
Saito et al.

[11] Patent Number: 5,421,984
[45] Date of Patent: Jun. 6, 1995

[54] OXYGEN CONCENTRATION SENSOR

[75] Inventors: Toshitaka Saito, Toyohashi; Masatoshi Suzuki, Nagoya; Hiromi Sano, Nagoya; Tomio Sugiyama, Nagoya; Satoru Nomura, Aichi, all of Japan

[73] Assignee: Nippondenso Co., Ltd., Kariya, Japan

[21] Appl. No.: 184,141

[22] Filed: Jan. 21, 1994

[30] Foreign Application Priority Data

Jan. 22, 1993 [JP] Japan .................................. 5-009192
Dec. 16, 1993 [JP] Japan .................................. 5-316635

[51] Int. Cl.$^6$ ............................................. G01N 27/26
[52] U.S. Cl. ..................................... 204/426; 204/424
[58] Field of Search ............... 204/424, 425, 426, 427, 204/428

[56] References Cited

U.S. PATENT DOCUMENTS 4,121,988 10/1978 Sano ..................................... 204/424
4,220,516 9/1980 Sano et al. ........................... 204/424

FOREIGN PATENT DOCUMENTS

| 53-29191 | 3/1978 | Japan . |
|---|---|---|
| 53-33194 | 3/1978 | Japan . |
| 54-97089 | 7/1979 | Japan . |
| 54-97490 | 8/1979 | Japan . |
| 3115966 | 5/1991 | Japan . |

Primary Examiner—Kathryn Gorgos
Assistant Examiner—Bruce F. Bell
Attorney, Agent, or Firm—Cushman, Darby & Cushman

[57] ABSTRACT

This invention aims at providing an oxygen concentration sensor having electrodes which are excellent in heat resistance and durability and maintain quick response. An electrode 26 on an exhaust side is formed on one of the side surfaces of a solid electrolyte 25, and an electrode 24 on an atmosphere side is formed on the other side surface. The electrode 26 on the exhaust side has a composite structure comprising a skeletal electrode 26a and a reaction electrode 26a. The skeletal electrode 26a has a film thickness of 5 to 20 μm and a porosity of less than 10%, and is a heat-resistant thick film for primarily forming a skeletal region. In contrast, the reaction electrode 26b has a film thickness of 0.5 to 2 μm and a porosity of 10 to 50%, and is a high response thin film for primarily forming a reaction region.

8 Claims, 7 Drawing Sheets

OXYGEN CONCENTRATION SENSOR

BACKGROUND OF THE INVENTION

1. Field of the Invention

This invention relates to an oxygen concentration sensor. More specifically, the present invention relates to an oxygen concentration sensor suitable for detecting an oxygen concentration in an exhaust gas of an internal combustion engine, for example.

2. Description of the Related Art

To produce an oxygen concentration sensor for detecting an oxygen concentration in an exhaust gas emitted from an internal combustion engine for an automobile, for example, methods of forming electrodes by non-electrolytic plating, vacuum deposition, screen printing, and so forth, have been known in the past.

Among them, the oxygen concentration sensors having the electrodes formed by non-electrolytic plating, vacuum deposition, etc., have the advantage that since the thickness of the electrodes is relatively small, the sensors can quickly cope with the change of the oxygen concentration in a gas to be measured and can detect the oxygen concentration.

In the oxygen concentration sensors having the electrodes formed by screen printing, on the other hand, screen printing is effected on a green sheet using a platinum paste, or the like, and a plurality of green sheets are simultaneously sintered. Accordingly, the thickness of the electrode becomes relatively great. In other words, the thickness of the electrode formed by screen printing is by 5 to 20 times greater than the thickness of the electrode formed by non-electrolytic plating, vacuum deposition, etc., and for this reason, the oxygen concentration sensors having the electrode formed by screen printing have high heat resistance.

However, since the electrode formed by screen printing has a relatively large thickness in the oxygen concentration sensor having such an electrode, a gas diffusion distance from the electrode surface to a three-phase boundary point (triple point) becomes great. Accordingly, there occurs the problem that diffusibility of the gas to be measured in the electrode is deteriorated and the response speed of the sensor drops, particularly remarkably at a low temperature.

To solve this problem, a method is known in the art in which ceramic powder, etc., are mixed into the platinum paste, to restrict sintering of the platinum particles during sintering, to thereby obtain a high porosity of the electrode. According to this method, however, the effect of the large thickness of the electrode is still great and the effect of improving the response is not so extreme.

SUMMARY OF THE INVENTION

The present invention was completed so as to solve the problem with the prior art described above, and is directed to providing an oxygen concentration sensor which not only is excellent in heat resistance and durability but also maintains a high response.

To accomplish the object described above, according to the construction of the first embodiment of the present invention, the measurement electrode is formed by two kinds of electrodes, that is, the first electrode and the second electrode. In the first embodiment of the present invention, when the first electrode is particularly formed as the skeletal region and the second electrode is particularly formed as the reaction region, the thickness of the first electrode is made greater than that of the second electrode and the porosity of the former is lower than that of the latter.

Accordingly, since the first electrode is so formed as to have a greater thickness than the second electrode, the first electrode has higher heat resistance than the second electrode. Nonetheless, because the second electrode is so formed as to have a relatively small film thickness but to have a greater porosity than the first electrode, the second electrode can secure higher response than the first electrode.

According to the construction of the second embodiment of the present invention, the second electrode has a smaller film thickness but higher response than the first electrode. Though the second electrode has lower heat resistance than the first electrode because its thickness is smaller than that of the latter, a higher response can be obtained.

In the constructions of the first and second embodiments of the present inventions, the combination of the first electrode with the second electrode can simultaneously realize both high heat resistance and high response, which are generally believed to be contradictory to each other.

As explained above, in the oxygen concentration sensor according to the present invention, the measurement electrode to be formed on one of the main surfaces of the solid electrolyte comprises the heat-resistant thick first electrode for primarily forming the skeletal region and the high response thin second electrode for primarily forming the reaction region, in the composite structure. Accordingly, the oxygen concentration sensor provides an excellent effect in that excellent heat resistance of the first electrode and excellent response of the second electrode can be fully exploited in combination.

These and other objects and novel features of the present invention will become more apparent from the following description when taken in conjunction with the accompanying drawings.

DESCRIPTION OF THE PREFERRED EMBODIMENTS

Hereinafter, preferred embodiments of the present invention will be described in detail with reference to the accompanying drawings.

Figure 1:
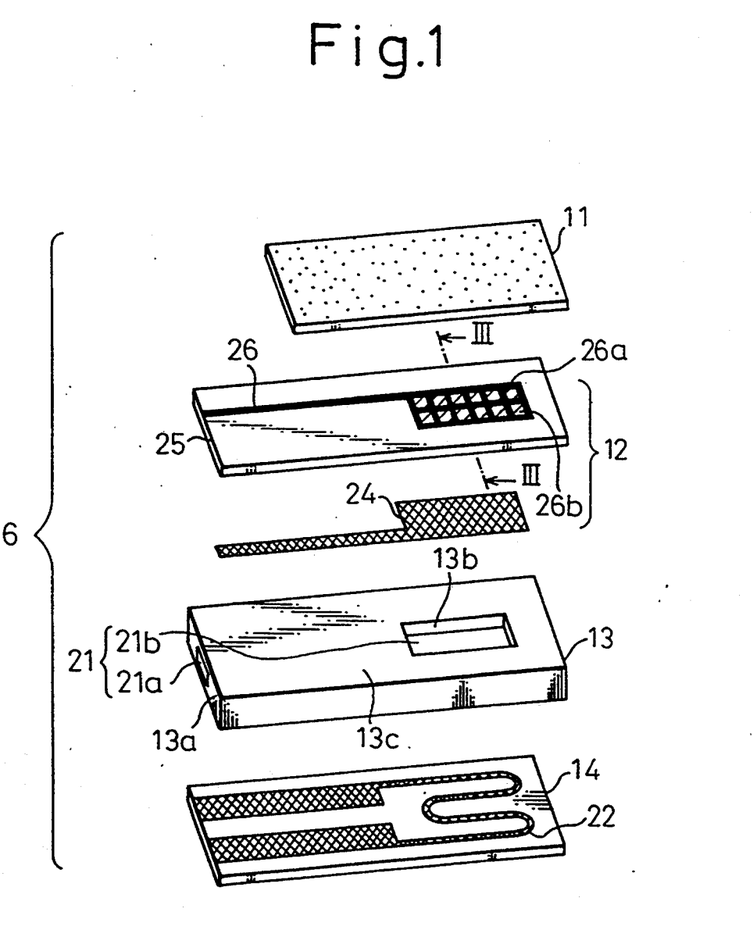
FIG. 1 is a schematic exploded perspective view of components of a sensor device according to the first example of the present invention.
Figure 2:
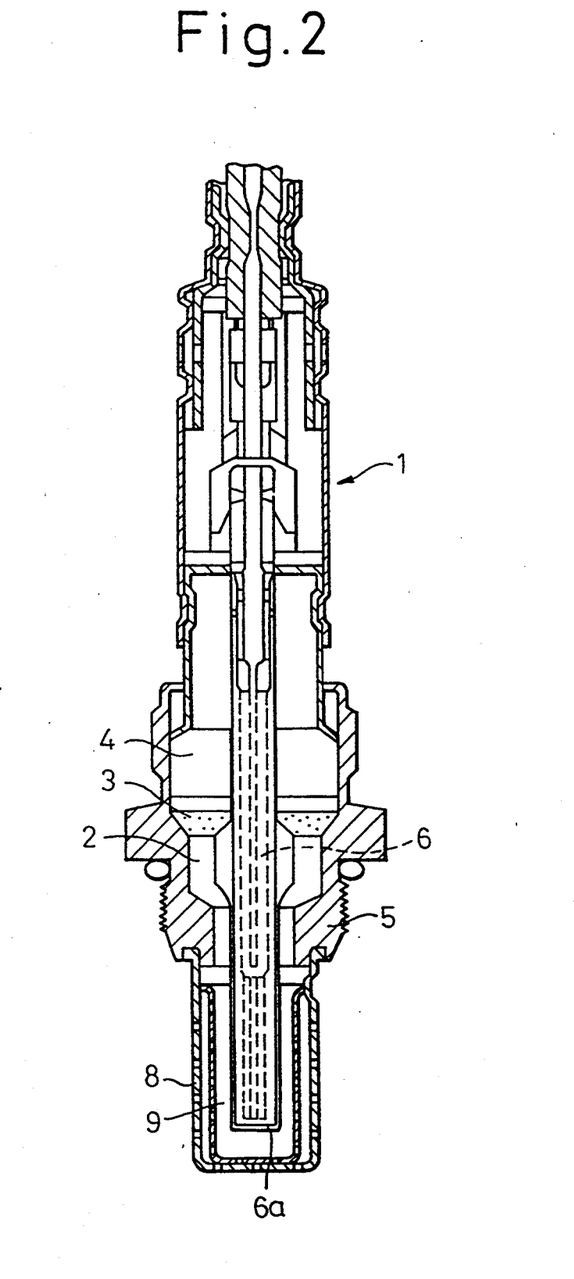
FIG. 2 is a sectional view showing an oxygen sensor to which the first example of the present invention is applied.
Figure 3:
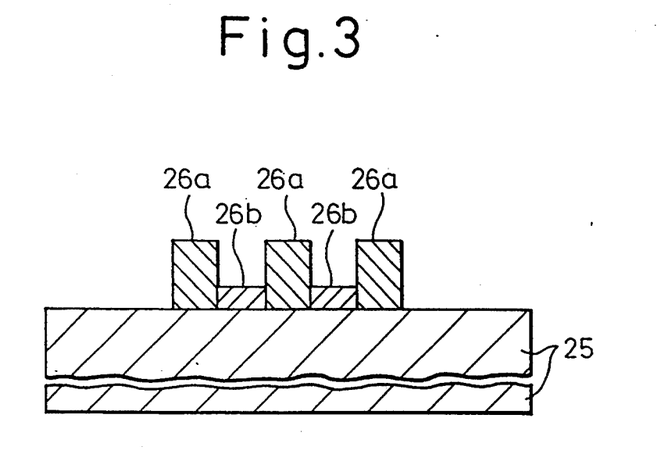
FIG. 3 is a sectional view taken along a line III—III of FIG. 1.

The first example of the present invention represents the application of the present invention to an oxygen concentration sensor made of zirconia shown in FIG. 2. FIG. 1 is an exploded view of the sensor device 6 shown in FIG. 2, and FIG. 3 is a schematic view as an enlarged sectional view of FIG. 1 taken along a line III—III thereof.

In FIG. 2, an oxygen sensor 1 equipped with talc 3 is formed by packing ceramic powder into the end portion of a holder 2 made of alumina. An insulator 4 made of alumina is put on this talc 3 in an axial direction, and a housing 5 is so fixed by caulking as to cover them from their outer surface. The distal end portion 6a of the sensor device 6 inserted into the central portion of the holder 2, and the talc 3 and the insulator 4 is covered with a cylindrical cover 8 having apertures and a bottom, through a space 9.

The exploded structure of the sensor device 6 is shown in a schematic exploded view of FIG. 1. In FIG. 1, the ceramic sensor 6 is produced by sequentially laminating a ceramic coating layer 11, an electrode portion 12, a substrate 13 and a ceramic sheet 14. In practice, the sensor device is formed when raw materials of the constituent elements of the sensor device 6 are simultaneously sintered. Hereinafter, each constituent element of the sensor device will be explained in sequence.

The substrate 13 is made of an insulating material such as $Al_2O_3$, $Si_3N_4$, etc. This is to secure an electrical insulation property between later-appearing platinum heater 22 and electrode portion 12. The substrate 13 includes therein an air inlet port 21 extending in an axial direction. One end 21a of this air inlet port 21 is open to the end face 13a of the substrate 13 while the other end 21b is open to the flat side surface 13c. This opening 21b is formed at a position facing an atmosphere side electrode 24 as a reference electrode which will be described below.

The electrode portion 12 comprises a thin sheet-like solid electrolyte 25 having one and other main surfaces opposing each other, the electrode 24 on the atmosphere side which is formed on one of the main surfaces of the solid electrolyte 25 as a reference electrode, and an electrode 26 on an exhaust side formed on the other main surface of the solid electrolyte 25 as a measurement electrode. The solid electrolyte 25 comprises an oxygen ion conductor of $ZrO_2$ doped with $Y_2O_3$, $Yb_2O_3$, or the like.

The electrode 26 on the exhaust side serves as the measurement electrode, and comprises a skeletal electrode 26a as a first electrode formed into a grid form, and a reaction electrode 26b as the second electrode packed into the gaps of the grid. The skeletal electrode 26a and the reaction electrode 26b are formed on the surface of the substrate 25 as shown in FIG. 3. Both of the skeletal electrode 26a and the reaction electrode 26b have predetermined levels of heat resistance and gas diffusibility, and high response. Further, the skeletal electrode 26a is relatively thick and more compact (dense) and has higher heat resistance than the reaction electrode 26b, while the reaction electrode 26b is relatively thin and more porous and has higher gas diffusibility and higher response than the skeletal electrode 26a.

The skeletal electrode 26a is from 5 to 20 $\mu$m thick, and has a porosity of less than 10% and more preferably from 2% to less than 10%. Since the film thickness is at least 5 $\mu$m, high heat resistance and high durability can be secured, and if the film thickness exceeds 20 $\mu$m, gas diffusibility drops remarkably.

The porosity is preferably at least 2% for the following reasons. If the porosity is less than 2%, gas permeability remarkably drops, and this porosity range is directed to secure the sensor function by the skeletal electrode, particularly when the reaction electrode is deteriorated after the use for a long time. The porosity must be less than 10%, because the skeletal electrode 26a becomes excessively porous and heat resistance drops if the porosity is greater than 10%.

Figure 4:
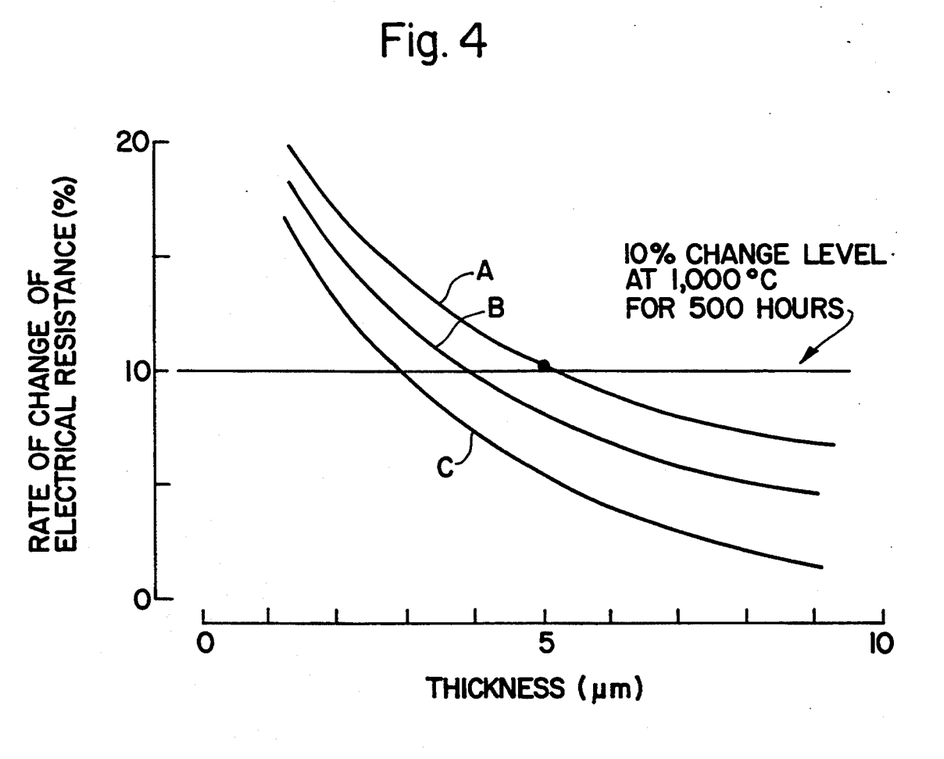
FIG. 4 is a characteristic diagram showing the relationship between a thickness and heat resistance when a porosity of a first electrode is changed.

FIG. 4 shows the result of measurement of the heat resistance of the skeletal electrodes with porosity of 2%, 6% and 10% while changing the thickness of the skeletal electrode. In this case, the skeletal electrodes having the porosity of 2%, 6% and 10% are called "A", "B" and "C" in FIG. 4, respectively.

As can be seen clearly from FIG. 4, the percent electric resistance change of the electrode with the thickness of 5 $\mu$m and the porosity of 10%, for example, exceeded 10% when the electrode was retained at 1,000° C. for 500 hours. This means that a problem occurs in the heat resistance when the oxygen concentration sensor is used at a high temperature, and it can be understood that good results are obtained when the porosity is less than 10% and preferably, from 2% to less than 10%.

The reaction electrode 26b preferably has a film thickness within the range of 0.5 to 5 $\mu$m and a porosity within the range of 10 to 50%. If the film thickness is less than 5 $\mu$m, the function of the electrode is likely to be impeded and when it exceeds 5 $\mu$m, sufficient response cannot be secured. The porosity must be at least 10% because, if it is less than 10%, gas permeability becomes insufficient. The porosity must be up to 50% because the heat resistance remarkably drops if it exceeds 50%.

Figure 5:
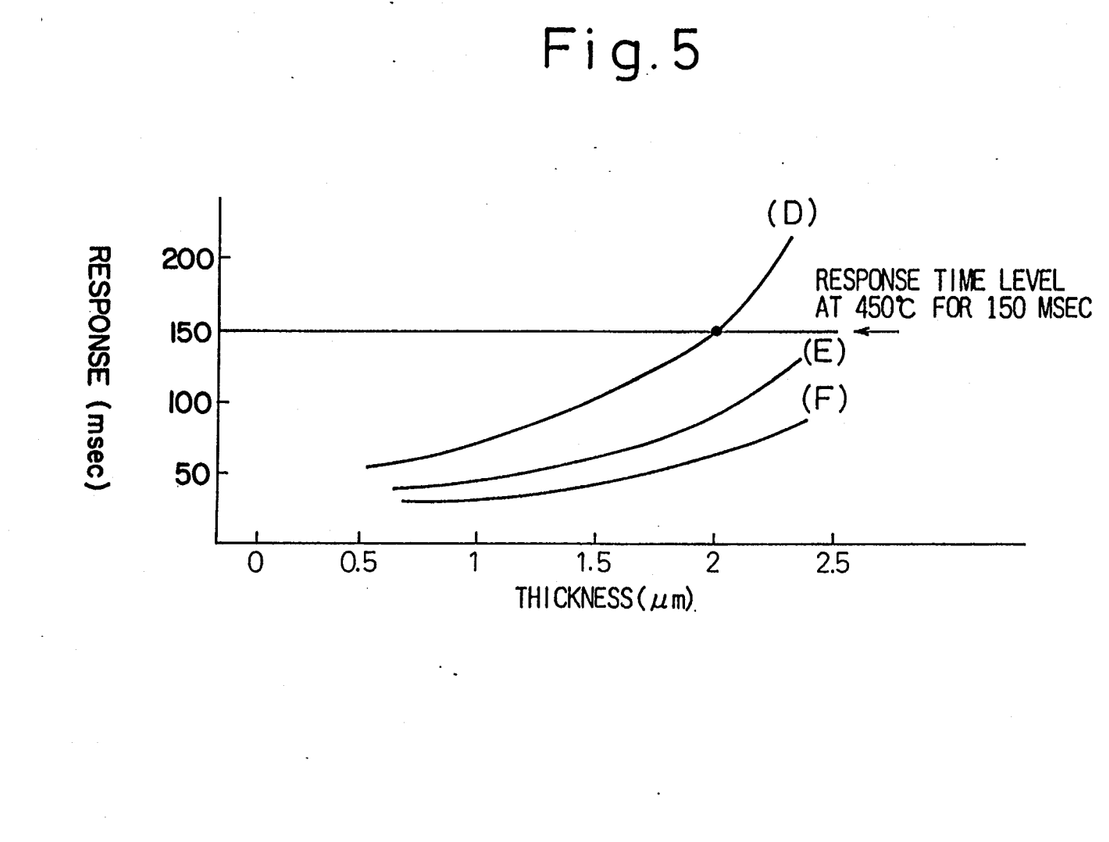
FIG. 5 is a characteristic diagram showing the relationship between the thickness and response when the porosity of a second electrode is changed.

FIG. 5 shows response when the thickness of the reaction electrode is changed at the porosity of 10%, 25% and 48%, respectively. The electrodes having the porosity of 10%, 25% and 48% are hereby called "D", "E" and "F", respectively.

As can be understood clearly from FIG. 5, the response time at the thickness of 2 $\mu$m and the porosity of 10% is about 150 msec. Accordingly, it can be understood that in order to secure a high response, it is necessary to increase the thickness of the electrode having a porosity of at least 10% and the thickness to 2 $\mu$m or more while avoiding densification of the electrode.

The area ratio of the skeletal electrode 26a to the reaction electrode 26b preferably satisfies the relation $0.1 \leq B/(A+B) \leq 0.5$, where A is the area of the skeletal electrode 26a and B is the area of the reaction electrode 26b. For, if $0.1 > B/(A+B)$, the characteristic properties brought forth by the reaction electrode, that is, high response, drops, and if $B/(A+B)>0.5$, heat resistance drops remarkably. In other words, high heat resistance and high response can be simultaneously satisfied within the range of $0.1 \leq B/(A+B) \leq 0.5$.

In FIG. 1, the ceramic coating layer 11 is made of alumina or the same material as the solid electrolyte 25, and is a gas-permeable coating film. The sensor of the present invention can be used as a potentiometric or polarographic sensor by suitably adjusting the porosity of this ceramic coating layer 11.

The ceramic sheet 14 is disposed on the surface of the substrate 13 opposite to the electrode portion 12. A heater 22 is formed on the surface of the ceramic sheet 14 opposing the substrate 13. To improve the heat resistance, the heater 22 is made of platinum to which ceramics powder such as alumina is added. The ceramic sheet 14 is made of the same material as that of the substrate 13, covers the heater 22 and protects it from poisoning from the exhaust gas.

Next, the production method of this sensor device 6 will be explained.

The method of producing the electrode is as follows. The skeletal electrode 26a and the reaction electrode 26b of the electrode 26 on the exhaust side, as the measurement electrode, are formed on the solid electrolyte sheet, composing the electrode portion 12, by screen printing or the like means, and the reference electrode 24 is likewise formed on the opposite surface of the solid electrolyte by screen printing, or the like means. Then, the ceramic coating layer 11 as the green sheet, the electrode portion 12, the substrate 13 and the ceramic sheet 14 are laminated, and are simultaneously sintered at 1,500° C. for one hour, for example. In this way, the sensor device 6 is formed. Particularly when the composite electrode 26 on the exhaust side is formed, a paste prepared by mixing platinum powder, an organic platinum material and an organic binder is used for screen printing in order to reduce the thickness of the reaction electrode 26b, and then a paste containing only platinum powder and an organic binder is used to print the skeletal electrode 26a with a large thickness.

Figure 6:
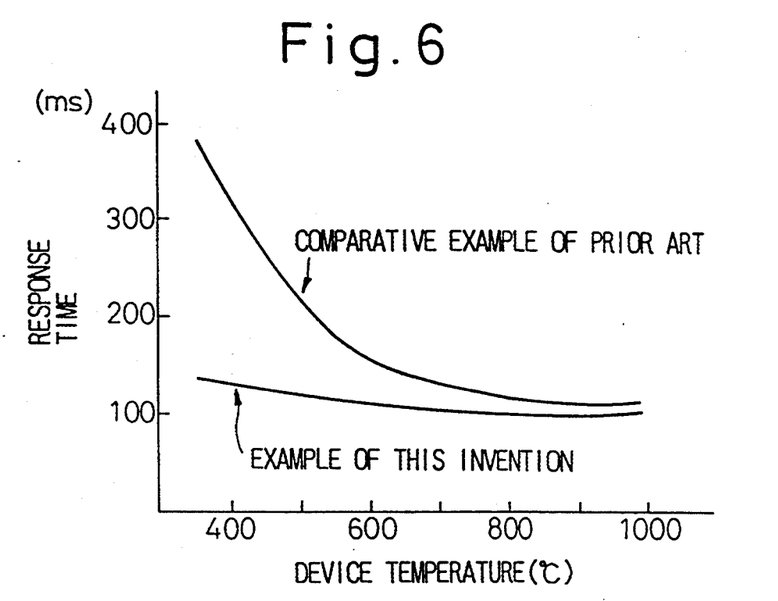
FIG. 6 is a characteristic diagram showing the relationship between a device temperature and a response time in the first example of the present invention in comparison with a prior art Comparative Example.
Figure 7:
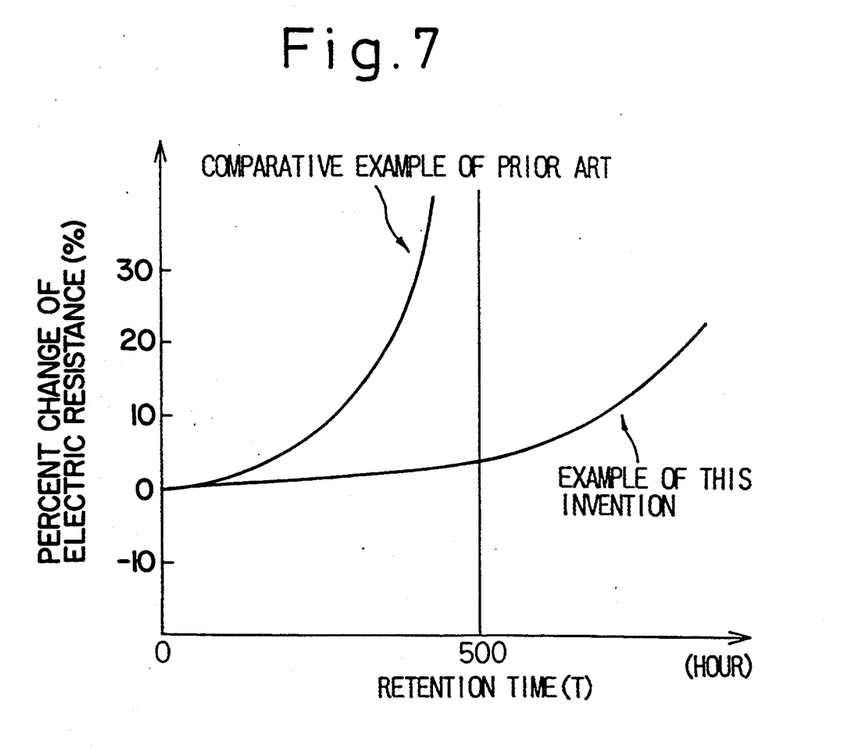
FIG. 7 is a characteristic diagram showing the relationship between a retention time under a high temperature condition and an electric resistance in the first example of the present invention in comparison with the prior art Comparative Example.

Next, experimental data are shown in FIGS. 6 and 7.

FIG. 6 demonstrates that the example of the present invention has a faster response than the prior art Comparative Example and FIG. 7 demonstrates that the example of the present invention has faster heat resistance than the prior art Comparative Example.

The response of the device to temperature is plotted on the abscissa as shown in FIG. 6 and the response time at each device temperature is measured. The result is shown in FIG. 6. It can be understood from this diagram that the example of the present invention has a faster response than the prior art Comparative Example particularly in a low temperature range of the device temperature.

As to the heat resistance, the change of the electric resistance R when the device is retained at 1,000° C. for 500 hours is compared as shown in FIG. 7. It can be understood from FIG. 7 that when the device is retained at 1,000° C. in the example of the present invention, the increase of the electric resistance s relatively low compared to the prior art Comparative Example for an extended period of time. In the Comparative Example of the prior art, the increase of the electric resistance is remarkable within a relatively short time.

Next, an example of the experimental result is tabulated in Table 1.

In this experiment, the heat resistance and response are evaluated by changing the porosity of each of the skeletal and reaction electrode, their thickness and the area ratio of the reaction electrode $[B/(A+B)]$. The evaluation standard is as follows. A response time of less than 150 msec at the temperature of 450° C. is judged as acceptable and a response time of not greater than 150 msec, is rejected. After the sensor devices as the testpieces are retained at 1,000° C. for 500 hours, those exhibiting the increase ratio of the electric resistance R of 10% or more are rejected and those having the increase ratio of less than 10%, are accepted. The results are tabulated in Table 1.

TABLE 1

| | skeletal structure | | reaction electrode | | | evaluation | |
|---|---|---|---|---|---|---|---|
| | porosity (%) | thickness (μm) | porosity (%) | thickness (μm) | reaction electrode ratio [B/(A + B)] | heat-resistance | response |
| Example 1 | 10 | 5 | 50 | 0.5 | 0.3 | fair | fair |
| 2 | 6 | 10 | 25 | 1 | 0.3 | " | " |
| 3 | 2 | 20 | 10 | 2 | 0.3 | " | " |
| Com. Ex. 1 | 20 | 2 | 5 | 5 | 0.3 | inferior | inferior |
| 2 | 6 | 2 | 25 | 5 | 0.3 | " | " |
| 3 | 20 | 10 | 5 | 1 | 0.3 | " | " |
| 4 | 6 | 10 | 25 | 5 | 0.3 | fair | " |
| 5 | 6 | 10 | 5 | 1 | 0.3 | " | " |
| 6 | 6 | 2 | 25 | 1 | 0.3 | inferior | fair |
| 7 | 20 | 10 | 25 | 1 | 0.3 | " | " |
| 8 | 6 | 10 | 25 | 1 | 0.05 | fair | inferior |
| 9 | 6 | 10 | 25 | 1 | 0.7 | inferior | fair |

As tabulated in Table 1, it has been found that both response and heat resistance are satisfactory when the film thickness of the skeletal structure is 50 to 20 μm, its porosity is less than 10%, the film thickness of the reaction electrode is 0.5 to 2 μm, its porosity is within the range of 10 to 50% and the area ratio $B/(A+B)$ of the reaction electrode is within the range of 0.1 to 0.5.

Figure 8:
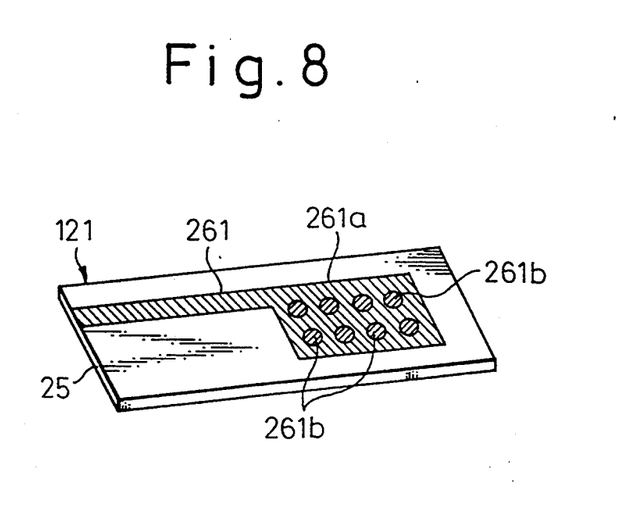
FIG. 8 is a schematic perspective view of a measurement electrode of the sensor device according to the second example of the present invention.
Figure 9:
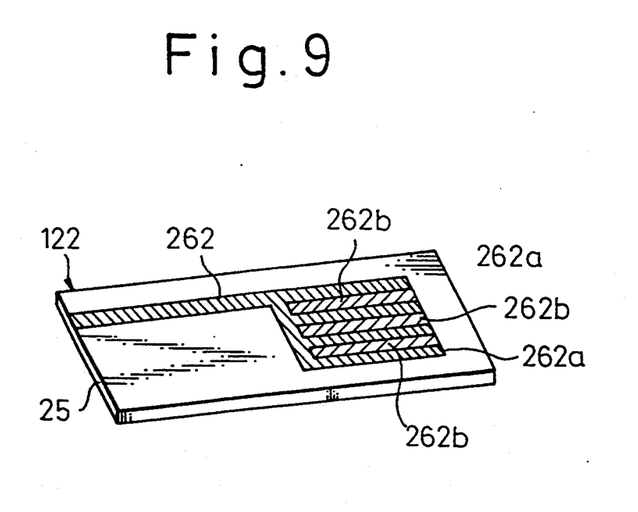
FIG. 9 is a schematic perspective view of the measurement electrode of the sensor device according to the third example of the present invention.
Figure 10:
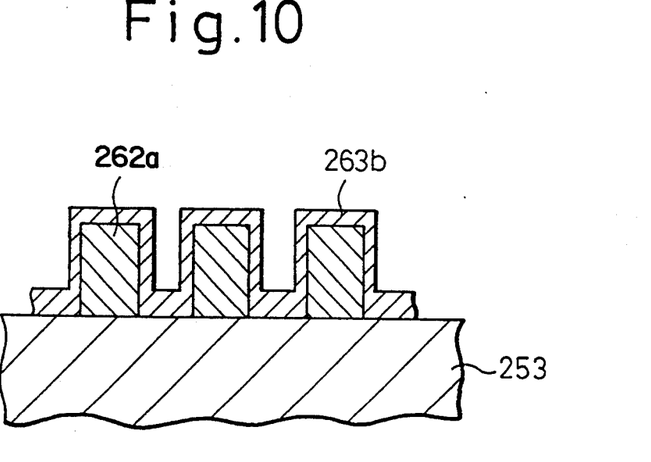
FIG. 10 is a schematic sectional view of the measurement electrode of the sensor device according to the fourth example of the present invention.

Next, examples of the modified patterns of the skeletal electrode and the reaction electrode of the electrode on the exhaust side of the sensor devices according to the second to fourth examples of the present invention are illustrated in FIGS. 8 to 10.

Reference numeral 122 denotes an electrode forming sheet. The electrode portion 121 in the second example shown in FIG. 8 represents an example where the reaction electrode 261b has a pattern of circles. In other words, the electrode 261 on the exhaust side, which is formed on one of the surfaces of the solid electrolyte 25, comprises the skeletal electrode 261a and the reaction electrode 261b. Since the material of the skeletal electrode 261a and the reaction electrode 261b is the same as that of the first example, the explanation will be omitted.

According to this second example, since the reaction electrode 261b has a pattern of circles, printing becomes easier on the green sheet of the solid electrolyte 25 before sintering of the sheet during the production.

The third example shown in FIG. 9 represents the example where the reaction electrode 262b is formed into a shape of slits. The electrode 262 on the exhaust side, which is formed on one of the surfaces of the solid electrolyte 25, has four teeth comb-like skeletal electrode 262a. The slit-like reaction electrodes 262b are formed between these skeletal electrodes 262a. In the present invention, the number of these skeletal electrodes 262a is not particularly limitative.

According to this third example, since the skeletal electrode 262a and the reaction electrodes 262b are formed into the slit-like shape, printing and formation of the skeletal electrodes and the reaction electrodes on the solid electrolyte green sheet becomes much easier than in the second example.

In the fourth example shown in FIG. 10, the reaction electrodes 263b as the second electrode may be formed on the solid electrolyte 253, which is the same as the solid electrolyte 25 in FIG. 3, in such a manner as to cover the skeletal electrodes 263a as the first electrode.

According to this structure, the contact between the skeletal structure 262a and the reaction electrodes 263b becomes more reliable and heat resistance as well as response are not lost. Furthermore, sputtering, etc., can be employed for the fabrication, and the electrodes can be produced more easily.

Figure 11:
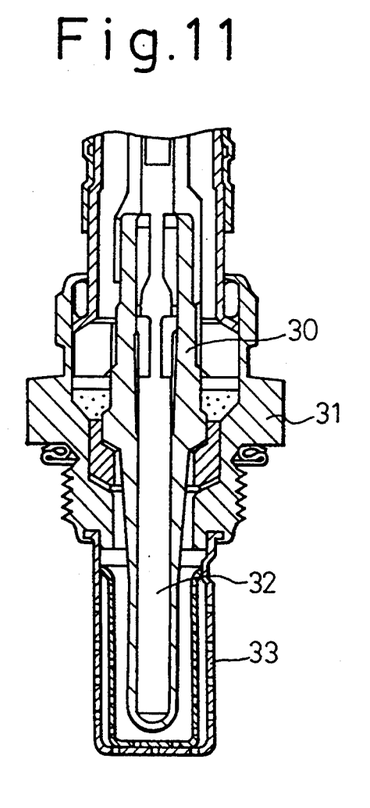
FIG. 11 is an explanatory view showing still another example of the present invention.

The foregoing examples illustrate the application of the present invention to the thin sheet-like solid electrolyte, but the present invention is not particularly limited thereto. For example, the solid electrolyte may be a cup-like solid electrolyte having mutually opposing side surfaces as shown in FIG. 11.

This cup-like solid electrolyte 30 is held by a housing 31. A heater 32 is disposed inside a solid electrolyte electric field chamber.

A reference electrode, not shown in the drawing, is disposed inside the cup-like solid electrolyte 30. The measurement electrode of the present invention, which comprises the first and second electrodes and is not shown in the drawing, is formed outside the solid electrolyte 30. A protective cover 33 is disposed in such a manner as to cover this measurement electrode.

At this time, the first and second electrodes are formed by a curve face printing method such as a pad printing method.

An oxygen concentration sensor having such a cup-like solid electrolyte can similarly provide the same effect as that of the first example.

The detection system is not particularly limited to the electromotive force system, either. In other words, the electrode structure of the present invention can of course be applied to an oxygen concentration sensor of a current detection system such as a pump current system and a limit current system for detecting an oxygen concentration over a broad range.

We claim:

1. An oxygen concentration sensor comprising:
   a solid electrolyte having first and second main surfaces opposite to each other;
   a reference electrode formed on the first main surface of the solid electrolyte; and
   a measurement electrode formed on the second main surface of the solid electrolyte, the measurement electrode having a composite structure of first and second electrodes, wherein there are a plurality of said second electrodes, said first electrode has a plurality of skeletal regions which surround said plurality of second electrodes, said plurality of second electrodes are electrically connected with each other through said skeletal regions of said first electrode, said plurality of skeletal regions of said first electrode are electrically connected with each other, the first electrode has a film thickness of 5 to 20 $\mu$m and a porosity of less than 10%, the second electrode has a film thickness of 0.5 to 2 $\mu$m and a porosity of 10 to 50%, each of said plurality of second electrodes is thinner than each of said plurality of skeletal regions of said first electrode, said plurality of second electrodes have a primary function of a sensor, and said skeletal regions of said first electrode have a primary function of as electrical connector between said plurality of second electrodes and a supplementary function of a sensor.

2. An oxygen concentration sensor according to claim 1, wherein said solid electrolyte is in the shape of a thin sheet.

3. An oxygen concentration sensor according to claim 1, wherein said solid electrolyte is in the shape of a cup.

4. An oxygen concentration sensor according to claim 1, wherein the total area A of said first electrode and the total area B of said second electrode satisfy the following relation:

$$0.1 \leq B/(A+B) \leq 0.5.$$

5. An oxygen sensor according to claim 1, wherein said plurality of skeletal regions of said first electrode are in the form of a grid having a plurality of spaces therein, and said plurality of second electrodes are formed in said spaces surrounded by the grid of the skeletal regions of said first electrode.

6. An oxygen sensor according to claim 1, wherein said plurality of second electrodes are in the form of plane circles and said plurality of skeletal regions of said first electrode are in the form surrounding the plane circles of said plurality of second electrodes.

7. An oxygen sensor according to claim 1, wherein said plurality of skeletal regions of said first electrode are in the form of a comb and said plurality of second electrodes are formed between fingers of the comb of said skeletal regions.

8. An oxygen sensor according to claim 1, wherein said second electrodes are also formed over the extension surfaces of said plurality of skeletal regions of said first electrode.

* * * * *